United States Patent [19]
Kaczmarzyk et al.

[11] 4,300,561
[45] Nov. 17, 1981

[54] EASILY REMOVABLE TAMPON

[75] Inventors: Leonard M. Kaczmarzyk; James J. Hlaban, both of Neenah; David M. Jackson, Appleton, all of Wis.

[73] Assignee: Kimberly-Clark Corporation, Neenah, Wis.

[21] Appl. No.: 86,808

[22] Filed: Oct. 22, 1979

[51] Int. Cl.³ .............................................. A61F 13/20
[52] U.S. Cl. ................................................... 128/285
[58] Field of Search ............... 128/270, 284, 285, 263, 128/296, 290

[56] References Cited
U.S. PATENT DOCUMENTS

| | | | |
|---|---|---|---|
| 3,683,912 | 8/1972 | Olson et al. | 128/285 |
| 3,902,493 | 9/1975 | Baier et al. | 128/285 |
| 4,056,103 | 11/1977 | Kaczmarzyk et al. | 128/285 |
| 4,134,863 | 1/1979 | Fanta et al. | 128/285 |

OTHER PUBLICATIONS

"The Extra Pharmacopoeia", Martindale, *The Pharmaceutical Press* (London), 27th Ed. 1972.
"A Consumers Dictionary of Cosmetic Ingredients", Winter, *Crown*, 1974.

*Primary Examiner*—Robert W. Michell
*Assistant Examiner*—T. J. Wallen
*Attorney, Agent, or Firm*—Howard Olevsky; William D. Herrick

[57] ABSTRACT

A tampon having a superabsorbent material included as part of its absorbent system and a moisture permeable outer wrapping. The outer wrap has an emollient covering a substantial portion to aid in withdrawal of the tampon without substantially affecting absorption of menstrual fluid.

4 Claims, No Drawings

1

EASILY REMOVABLE TAMPON

FIELD OF THE INVENTION

This invention relate to a tampon and particularly one containing a superabsorbent material.

BACKGROUND OF THE INVENTION

Recently, tampons have been utilized which contain superabsorbent materials. These materials are usually polymeric in nature and have a greater capacity for absorption of fluid per unit weight than the cotton or rayon fibers which have previously been traditionally used in tampons. The increase in fluid capacity and capillary suction pressure exhibited by the superabsorbent materials is such that only minor amounts, i.e. between 5 and 30 percent by weight are needed when used with conventional cotton or rayon fibers to provide vastly improved capacity and better absorptive efficiency per unit weight. These improved tampons may be worn for substantially longer time than tampons without superabsorbent.

One noticeable shortcoming of these higher capacity tampons not experienced with tampon products free of superabsorbents is the fact that withdrawal of the used tampon exhibits substantially greater frictional drag. Various attempts at reducing the frictional drag have taken the form of reducing the bulk of the tampon, providing a softer, lower density and less compressed tampon pledget, isolating the superabsorbent material in the tampon interior, tapering the withdrawal end of the tampon, using smoother wrapper material to reduce friction and a wrapper which retains part of the menstrual fluid at the surface to aid in withdrawal. Also, U.S. Pat. Nos. 2,340,311; 2,734,505; and 2,854,978 disclose utilizing surfactants as insertion aids for the traditional, non-superabsorbent-containing tampons. These surfactants may be utilized either for purposes of chemically reacting with the menstrual fluid or in conjunction with solid waxy lubricants. The surfactants disclosed in the above patents are either of the soap class, i.e. alkali metal salts of fatty acids, alcohols, sulphonated alcohols, etc.; quaternary ammonium salts; alkanol amines; or short chain polyhydric alcohols.

In U.S. Pat. No. 2,340,311 a coating is provided to aid in retention of the absorbent material in a compressed form as well as to facilitate tampon insertion. The coating includes a film forming substance to provide the binding effect which is strong enough to resist the expansive force of the compressed material and is water dispersible so that "it can readily dissolve in the body fluids, especially in the presence of surface tension depressant". The coating may also have a surface active agent used to depress the surface tension of the fluids and the surface active agents described include a quaternary ammonium salt and several other conventional surfactants such as polyhydric alcohols. Other polyhydric alcohols may be present as a plasticizer. Since this particular patent utilizes the primary insertion aid matrix as a binding material the disclosure states that it must be solid at room temperature and rapidly dispersible after contact with fluid.

U.S. Pat. No. 2,854,978 describes the utilization of a foamed material to provide a slippery surface for ease of insertion. These foams are designed to be of a water dispersible solid having a surface active agent. The foams are set forth as a solid separate component which is distinct from the tampon absorptive surface and is considered a separate element which does not interact with the absorptive part of the tampon.

U.S. Pat. No. 2,734,505 describes a tampon having a two component covering at its leading edge. One component is a water dispersible surface active agent and between the surface active agent and the tampon is a covering layer which blocks the passage of moisture to the tampon body.

Prior art lubricants can therefore be summarized in the following manner. First, there is a class of solid so-called "insertion aids" which may or may not contain surfactant. These solid generally wax-like insertion aids are designed to aid in the insertion of the tampon and either dissipate rapidly when subjected to exposure to menstrual fluid or interfere with the absorptive function of the tampon itself due to the barrier properties associated with the solid material. These particular approaches would provide disadvantages when used to inhibit super absorption suction pressure because either they would dissipate completely with the menstrual fluid being therefore unavailable at withdrawal or they would interfere with fluid uptake due to the nature of the covering itself.

SUMMARY OF THE INVENTION

It has now been found that by coating a tampon having a fluid permeable outer wrapping and a superabsorbent as part of the absorptive material with an emollient which is a liquid at ambient temperature, lubrication of the tampon during withdrawal is established, by reducing frictional drag suction pressure associated with superabsorbents is reduced and there is substantially no interference with the absorptive function of the tampon itself. Actual use comparison tests have shown that the tampon of this invention significantly improves ease of removal when compared with a tampon of identical composition without emollient.

For purposes of this invention the absorbent core contains superabsorbent particulate material in either fibrous or nonfibrous form in an amount sufficient to provide a tampon of enhanced fluid holding capacity per unit weight. A superabsorbent material, for purposes of this invention, is defined as one which has a capillary suction pressure of at least 25 cm of $H_2O$ when a gram of such material has absorbed 5 ml of physiological saline solution.

An emollient is defined in Webster's New Collegiate Dictionary, 7th Edition, G & C Merriam Co., Springfield, Massachusetts as a material which is characterized by "making soft or supple; soothing especially to the skin or mucous membranes". As set forth in the *McCutcheon's* 1979 *Annual of Functional Materials,* Manufacturing Confectioners Publishing Company, Rock Road, Glen Rock, New Jersey, 1979, an emollient is of one of the following chemical classes: long chain alcohols, generally greater than C-14; fatty acids/fatty alcohol ester with and without poly ether bridges; and oil e.g. petrolatum, castor oil, vegetable oils in general. For purposes of this invention the emollients must be liquid at ambient temperatures.

For purposes of this invention, emollient is present at a level of 0.5% to 25% by weight of the cover material. It has even been found that slight levels of emollient provide some benefit in reducing frictional drag. Also, at the higher levels of emollient, there is a slight decrease in the amount of absorption with little perceivable increase in the ease of withdrawal. Generally therefore levels of emollient of 5 to 15% are preferred depending of course on the cover material and emollient utilized for the particular tampon. As will be seen in the Examples below certain cover materials offer less frictional resistance and therefore lower amounts of emollient can be used.

For purposes of this invention any fluid permeable outer wrap can be utilized. The art is replete with examples of suitable outer wraps used both in tampons and also for sanitary napkins and conventional commercial and comfort considerations will generally provide the basis for choosing a particular wrap.

The effect on absorptive characteristics of tampons of the emollients of this invention are demonstrated in accordance with the procedure set forth in Example 1 below.

EXAMPLE 1

According to this Example, a commercially available tampon containing 20% AQUALON superabsorbent was tested in a syngina. (AQUALON is a trademark of Hercules Inc., Wilmington, Delaware.) A syngina is an artificial device utilized to simulate a vagina and well known to persons in the tampon art. It consists of a thin rubber membrane which holds the tampon. The membrane is within an outer case such that air can be introduced between the membrane and the outer case building up a pneumatic pressure on the exterior of the membrane, and the tube entering the membrane at its top end such that the tube orifice in the membrane simulates the entry to the exit from the cervix. A reservoir of syngina fluid is connected to the tube with a flow regulator such that it can be admitted to the membrane through the tube at a known and variable rate. The syngina fluid utilized was an artificial fluid having a salinity equal to menstrual fluid and has 0.1 gm. of PLURONIC F-68 per 2000 ml. of solution as a surfactant. PLURONIC is a trademark of BASF Wyandotte, Wyandotte, Michigan. The pneumatic pressure head is constant in a static syngina which was used for this Example and the pressure head had a value of 0.45 psi.

The results of the absorption test are indicated in the table below.

TABLE I

LABORATORY SYNGINA DATA
(Super KOTEX Tube Tampon with 20% AQUALON)

| Lubricant | % Add-on to Cover | Cover Material | Average Syngina Absorbency (Grams) | Average Tampon Weight |
|---|---|---|---|---|
| None (Control) | None | 8 × 5 scrim with double weight rayon applique (10 grams/yd$^2$) | 16.30 | 4.12 |
| None (Control) | None | spunbonded polypropylene (13 grams/yd$^2$) | 16.65 | 4.05 |
| Standamul 1414E | 10% | spunbonded polypropylene (13 grams/yd$^2$) | 16.06 | 4.07 |
| Propal | 1.7% | spunbonded polypropylene (13 grams/yd$^2$) | 16.45 | 4.09 |
| Standamul HE | 8.5% | spunbonded polypropylene (13 grams/yd$^2$) | 16.23 | 4.07 |

STANDAMUL is a trademark of Henkel, Inc. of New York, New York and STANDAMUL 1414E is a myreth-3 myristate while STANDAMUL HE is a glycereth polyethoxy cocoate. PROPAL is isopropyl palmitate and is a trademark of Robinson-Wagner Company of Mamaroneck, New York.

As can be seen from the table above, there is virtually no effect on absorptive capacity resulting from the addition of these liquid emollients.

EXAMPLE 2

This Example is designed to show the effect of the emollients of this invention on the force needed for removal of the tampon. To accomplish this, a frictional force test procedure was set up in the following manner. A sample of the cover material containing emollient was placed over a batt of tampon absorbent material. A test sled in the form of a disc was prepared and placed on the cover sample. The test sled was 5 cm. in diameter and is in the form of a disc. A blotter is located directly under the disc and is moistened and a pig intestine segment is stretched over the disc to simulate vaginal tissue. The weight of the disc assembly was 100 gm. The sled is attached to an Instron unit which records a frictional force curve as the sled is pulled over the cover sample. The Instron unit was operated at a speed of 50 cm/minute with a chart speed of 5 cm/minute. Peak forces for each sample were computed and averaged with all other force readings for each sample according to the table below.

TABLE II

LABORATORY FRICTIONAL FORCE DATA
(Without Weight on Sample)

| Lubricant | % Add-on to Cover | Cover Material | Measured Peak Frictional Force (grams) |
|---|---|---|---|
| None (Control) | None | 8 × 5 scrim with double weight rayon applique (10 grams/yd$^2$) | 303 |
| None (Control) | None | spunbonded polypropylene (13 grams/yd$^2$) | 214 |
| Standamul 1414E | 10% | spunbonded polypropylene (13 grams/yd$^2$) | 129 |
| Propal | 1.5% | spunbonded polypropylene (13 grams/yd$^2$) | 89 |
| Standamul HE | 4.0% | scrim with double rayon applique | 234 |
| Standamul HE | 8.5% | spunbonded polypropylene (13 grams/yd$^2$) | 107 |

As can be seen from the above table, the emollients of the subject invention reduce frictional drag regardless of the particular choice of cover material and in each instance the frictional drag is reduced a significant amount.

EXAMPLE 3

The procedure for Example 2 is repeated except a 1000 gram weight was placed on the test disc. The results are indicated in the table below.

TABLE III

LABORATORY FRICTIONAL FORCE DATA
(With 1000 gram Weight on Sled)

| Lubricant | % Add-on to Cover | Cover Material | *Average Measured Peak Frictional Force (grams) |
|---|---|---|---|
| None | None | 8 × 5 scrim with double weight | 618 |

TABLE III-continued

LABORATORY FRICTIONAL FORCE DATA
(With 1000 gram Weight on Sled)

| Lubricant | % Add-on to Cover | Cover Material | *Average Measured Peak Frictional Force (grams) |
|---|---|---|---|
| None | None | rayon applique (10 grams/yd$^2$) spunbonded polypropylene (13 grams/yd$^2$) | 413 |
| Standamul 1414E | 15% | spunbonded polypropylene (13 grams/yd$^2$) | 163 |

*Modified Instron Test with .4 psi weight on sled (1000 gram is equal to 0.4 psi on sled.)

Using a weighted test sled more closely simulates active movements encountered during the use of a tampon. Pressure on the tampon results from the activities associated with normal movement and the added weight is designed to simulate these added forces.

What is claimed is:

1. A tampon having a fluid permeable cover and an emollient covering substantially the entire surface of the cover which is liquid at room temperature and coated on the surface of the cover said coating selected from the group consisting of myreth-3 myristate, glycereth polyethoxy cocoate, and isopropyl palmitate, said permeable cover having an absorbent compound therein.

2. The tampon of claim 1 in which the superabsorbent material is present at an amount of from 1 to 30%.

3. The tampon of claim 1 in which the emollient is present at a level of 0.5 to 25% by weight of the cover material.

4. The tampon of claim 1 in which the cover material is spunbonded polypropylene.

* * * * *